US010444126B2

(12) United States Patent
Darfler et al.

(10) Patent No.: US 10,444,126 B2
(45) Date of Patent: *Oct. 15, 2019

(54) LIQUID TISSUE PREPARATION FROM HISTOPATHOLOGICALLY PROCESSED BIOLOGICAL SAMPLES, TISSUES AND CELLS

(71) Applicant: Expression Pathology, Inc., Rockville, MD (US)

(72) Inventors: Marlene M. Darfler, Gaithersburg, MD (US); David B. Krizman, Gaithersburg, MD (US)

(73) Assignee: EXPRESSION PATHOLOGY, INC., Rockville, MD (US)

( * ) Notice: Subject to any disclaimer, the term of this patent is extended or adjusted under 35 U.S.C. 154(b) by 152 days.

This patent is subject to a terminal disclaimer.

(21) Appl. No.: 14/868,812

(22) Filed: Sep. 29, 2015

(65) Prior Publication Data

US 2016/0018304 A1   Jan. 21, 2016

Related U.S. Application Data

(63) Continuation of application No. 13/896,778, filed on May 17, 2013, now Pat. No. 9,163,275, which is a continuation of application No. 12/348,868, filed on Jan. 5, 2009, now Pat. No. 8,455,215, which is a continuation of application No. 10/796,288, filed on Mar. 10, 2004, now Pat. No. 7,473,532.

(60) Provisional application No. 60/452,956, filed on Mar. 10, 2003.

(51) Int. Cl.

| C12Q 1/37 | (2006.01) |
|---|---|
| G01N 1/30 | (2006.01) |
| G01N 1/40 | (2006.01) |
| G01N 1/44 | (2006.01) |
| C12N 15/10 | (2006.01) |

(52) U.S. Cl.
CPC ....... *G01N 1/4044* (2013.01); *C12N 15/1003* (2013.01); *C12Q 1/37* (2013.01); *G01N 1/44* (2013.01); *G01N 1/30* (2013.01)

(58) Field of Classification Search
None
See application file for complete search history.

(56) References Cited

U.S. PATENT DOCUMENTS

| 5,225,325 A | 7/1993 | Miller et al. |
|---|---|---|
| 5,424,208 A | 6/1995 | Lee et al. |
| 5,672,696 A | 9/1997 | Wang et al. |
| 5,763,202 A | 6/1998 | Horoszelvicz |
| 5,843,657 A | 12/1998 | Liotta et al. |
| 6,251,467 B1 | 6/2001 | Liotta et al. |
| 6,274,309 B1 | 8/2001 | Kolesnick et al. |
| 6,469,159 B1 | 10/2002 | Belly et al. |
| 6,610,488 B2 | 8/2003 | Danenberg et al. |
| 6,833,270 B2 | 12/2004 | Poo et al. |
| 7,473,532 B2 * | 1/2009 | Darfler ............... C12N 15/1003 435/378 |
| 8,455,215 B2 * | 6/2013 | Darfler ............... C12N 15/1003 435/23 |
| 9,163,275 B2 * | 10/2015 | Darfler ............... C12N 15/1003 |
| 2001/0029018 A1 | 10/2001 | Danenberg et al. |
| 2003/0152987 A1 | 8/2003 | Cohen et al. |
| 2003/0170617 A1 | 9/2003 | Pasloske |
| 2004/0161645 A1 | 8/2004 | Poo et al. |
| 2005/0009045 A1 | 1/2005 | Greenfield et al. |
| 2005/0014203 A1 | 1/2005 | Darfler et al. |
| 2005/0059054 A1 | 3/2005 | Conrad et al. |
| 2005/0100944 A1 | 5/2005 | Cohen et al. |
| 2005/0130121 A1 | 6/2005 | Chong Conklin et al. |
| 2005/0164388 A1 | 7/2005 | Son et al. |

FOREIGN PATENT DOCUMENTS

| DE | 19963198 A1 | 9/2001 |
|---|---|---|
| EP | 0692533 A1 | 1/1996 |
| WO | 2002/046463 A2 | 6/2002 |

OTHER PUBLICATIONS

Ikeda et al. 1998. Extraction and Analysis of Diagnostically Useful Proteins from Formalin-fixed, Paraffin-embedded Tissue Sections. J Histochem. Cytochem, vol. 46, No. 3, pp. 397-403.*
Banerjee et al.1995. Microwave-Based DNA Extraction from Paraffin Embedded Tissue for PCR Amplificaion. Biotechniques, vol. 18, No. 5, pp. 768, 770, 772, 774.*
Banerjee et al., "Microwave-Based DNA Extraction from Paraffin Embedded Tissue for PCR Amplification", Biotechniques, 18(5): 768-770 (1995).
Bielawski, K., et al., "The suitability of DNA extracted from formalin fixed, paraffin-embedded tissues for double differential polymerase chain reaction analysis", International Journal of Molecular Medicine, 8: 573-578 (2001).
Bock, et al., "One-Step Extraction of RNA from Archival Biopsies", Analytical Biochemistry, 295(1): 116-117 (2001).
Brooks, S., et al,, "Release and analysis of polypeptides and glycopoiypeptides from formalin-fixed, paraffin wax-embedded tissue", Histochemical Journal, 30: 609-615 (1998).
Conlon, H., et al., "Irmnobi:ization of Enzymes in Polymer Supports", Journal of Chemical Education, 63(4): 368-370 (1986).
Coombs, N. J.; et al., "Optimisation of DNA and RNA extraction from archival formalin-fixed tissue", Nucleic Acids Research, 27(16): i-iii (1999).
Dwek, M.V., et al., "Oligosaccharide Release from Frozen and Paraffin-Wax-Embedded Archival Tissues", Analytical Biochemistry, 242: 8-14 (1996).

(Continued)

*Primary Examiner* — Blaine Lankford
(74) *Attorney, Agent, or Firm* — Harness, Dickey & Pierce, P.L.C.

(57) ABSTRACT

Methods are provided for directly converting histopathologically processed biological samples, tissues, and cells into a multiuse biomolecule lysate. This method allows for simultaneous extraction, isolation, solubilization, and storage of all biomolecules contained within the histopathologically processed biological sample, thereby forming a representative library of said sample. This multi-use biomolecule lysate is dilutable, soluble, capable of being fractionated, and used in biochemical assays.

9 Claims, 3 Drawing Sheets

(56) References Cited

OTHER PUBLICATIONS

Francis, G., et al., "Distribution and Partial Purification of a Liver Membrane Protein Capable of Inactivating Cytosol Enzymes", Biochem, J., 186: 571-579 (1980).

Gillespie, J., et. al., "Evaluation of Non-Formalin Tissue Fixation for Molecular Profiling Studies", American Journal of Pathology, 160(2): 449-457 (2002).

Hikaru I., et al., "Analysis of cyclin D1 and CDK expression in colonic polyps containing neoplastic foci: A study of proteins extracted from paraffin sections", Oncology Reports, 9: 1313-1318 (2002).

Ikeda, K., et al., "Extraction and Analysis of Diagnostically Useful Proteins from Formalin-fixed, Paraffin-embedded Tissue Sections", The Journal of Histochemistry & Cytochemistry, 46(3): 397-403 (1998).

International Preliminary Report on Patentability in PCT/US2004/007142 dated Sep. 16, 2005.

International Search Report in PCT/US2004/007142 dated Jan. 14, 2005.

Izawa, H., et al., "Analysis of cyclin D1 and CDK expression in colonic polyps containing neoplastic foci: A study of proteins extracted from paraffin sections", Oncology Reports, 9: 1313-1318 (2002).

Kanai, K., et al., "Variations in effectiveness of antigen retrieval pretreatments for diagnostic immunohistochemistry", Res. Vet. Sci. 64: 57-61 (1998).

Kaplan, B., et al, "Microextraction and Purification Techniques Applicable to Chemical Characterization of Amyloid Proteins in Minute Amounts of Tissue", Methods in Enzymology, 309: 67-81 (1999).

Kaplan, B., et al., "Micropurification techniques in the analysis of amyloid proteins", J. Clin. Pathol., 56: 66-90 (2003).

Lee, K., et al., "Proteornics: a technology-driven and technology-limited discovery science", Trends in Biotechnology, 9(6): 217-222 (2001).

Lehmann, U., et al., "Quantitative Molecular Analysis of Laser-Microdissected Paraffin-Embedded Human Tissues", Pathobiology, 68: 202-208 (2000).

Lehmann, U., et al., "Real-Time PCR Analysis of DNA and RNA Extracted from Formalin-Fixed and Paraffin-Embedded Biopsies", Methods, 25: 409-418 (2001).

Lewis, F., et al., "Unlocking the archive—gene expression in paraffin-e eddded tissue", Journal of Pathology, 195: 66-71 (2001).

MacIntyre, N., et al., "Unmasking antigens for immunohistochemistry", British Journal of Biomedical Science, 58: 190-196 (2001).

McCormack, A., et al., "Direct Analysis and identification of Proteins in Mixtures by LC/MS/MS and Database Searching at the Low-Ferntornole Level", Analytical Chemistry, 69: 767-776 (1997).

Merriam Webster Dictionary, © 2015 Merriam-Webster, incorporated, 3 pages.

Miyaji, T., et al., "Frozen Protein Arrays: A new method for arraying and detecting recombinant and native tissue proteins", Proteomics, 2: 1489-1493 (2002).

Muhlberg, A., et al., "Domain structure and intramolecular regulation of dynamin GTPase", The EMBO Journal, 16(22): 6676-6683 (1997).

Murff, C., et al., "A Sirnpie Experimetal Model to Isolate Antigenic Epitopes Recognized by Anitibodies", Bioscene, 24 (1): 11-15 (1998).

Office Action dated Jul. 1, 2006 issued in U.S. Appl. No. 10/796,288.

Office Action dated Aug. 10, 2007 issued in U.S. Appl. No. 10/796,288.

Office Action dated May 10, 2012 issued in U.S. Appl. No. 12/348,868.

Office Action dated Jan. 16, 2015 issued in U.S. Appl. No. 13/896,778.

Office Action dated Feb. 25, 2008 issued in U.S. Appl. No. 10/796,288.

Office Action dated Feb. 27, 2007 issued in U.S. Appl. No. 10/796,288.

Office Action dated Apr. 7, 2014 issued in U.S. Appl. No. 13/896,778.

Overton, W., et al., "Method to Make Paraffin-Embedded Breast and Lymph Tissue Mimic Fresh Tissue in DNA Analysis", Cytometry (Communications in Clinical Cytometry), 26: 166-171 (1996).

Overton, W., et al., "Reversing the Effect of Formalin on the Binding of Porpidium Iodide to DNA", Cytometry, 16: 351-356 (1994).

Paweletz, C., et al., "Reverse phase protein microarrays which capture disease progression show activation of pro-survival pathways at the cancer invasion front", Oncogene, 20: 1981-1989 (2001).

Petricoin, E., et al., "Clinical Proteomics: Translating Benchside Promise into Bedside Reality", Nature Reviews-Drug Delivery, 1: 683-695 (2002).

Schubert, E., et al., "Single Nucleotide Polymorphism Array Analysis of Flow-Sorted Epithelial Cells from Frozen Versus Fixed Tissues for Whole Genome Analysis of Allelic Loss in Breast Cancer", American Journal of Pathology; 160(1): 73-79 (2002).

Shedlock, A., et al., "Enhanced DNA Extraction and PCR Amplification of Mitochondrial Genes from Formalin-Fixed Museum Specimens", BioTechniqeus, 22(3): 394-400 (1997).

Shi, Shan-Rong, et al., "Antigen Retreival Techniques: Current Perspectives", The Journal of Histochemistry & Cytochemistry, 49(8): 931-937 (2001).

Shi, Shan-Rong, et al., "Antigen Retreival in Formalin-fixed, Paraffin-embedded Tissues: An Enhancement Method for Immunohistochemical Staining Based on Microwave Oven Heating of Tissue Sections", The Journal of Histochemistry & Cytochemistry, 39(6): 741-748 (1991).

Shi, Shang-Rung, et al., "Antigen Retrieval Technique: A Novel Approach to Immunohistochemistry on Routinely Processed Tissue Sections", The Journal of Histochemistry & Cytochemistry, Cell Vision, 2(1): 6-22 (1995).

Shi, Shang-Rong, et al., "DNA Extraction from Archival Formalin-fixed, Paraffin-embedded Tissue Sections Based on the Antigen Retrieval Principal: Heating Under the Influence of pH", The Journal of Histochemistry & Cytochernisty, 50 (8): 1005-1011 (2002).

Shi, Shang-Rong., et al., "Antigen Retrieval immunohistochemistry: Past, Present, and Future", The Journal of Histochemistry & Cytochemistry, 45(3): 327-343 (1997).

Sompuram, S., et al., "A Molecular Mechanism of Formalin Fixation and Antigen Retrieval", Am, J. Clin. Pathol., 121: 190-199 (2004).

Specht, et al., "Quantitative Gene Expression Analysis in Micordissected Archival Forrnalin-Fixed and Paraffin-Embedded Tumor Tissue", American Journal of Pathology, 158(2): 419-429 (2001).

Stollar, B., et al., "Immunochemical Approaches to Gene Probe Assays", Analytical Biochemistry, 161: 387-394 (1987).

Supplemental European Search Report in EP 04719188 dated Aug. 10, 2007.

Takehiko, M., et al., "Frozen Protein Arrays: A new method for arraying and detecting recombinant arid native tissue proteins", Proteomics, 2: 1489-1493 (2002).

Weizsäcker, F., et al., "A simple and rapid method for the detection of RNA in formalin-fixed, paraffin-embedded issues by PCR amplification", Biochemical Biophysical Research Communications, 174(1): 176-180 (1991).

Yumiko, N., et al, "The Quality of DNA Recovered from the Archival Tissues of Atomic Bomb Survivors is Good Enough for the Single Nucleotide Polymorphism Analysis in Spite of the Decade-long Preservation in Formalin", J. Radial Res., 43: 65-75 (2002).

* cited by examiner

Lane 1. Total genomic control DNA
Lane 2. Fraction 1: contains DNA
Lane 3. Fraction 2: contains protein in usual *Liquid Tissue™ preparation*

LIQUID TISSUE PREPARATION FROM HISTOPATHOLOGICALLY PROCESSED BIOLOGICAL SAMPLES, TISSUES AND CELLS

CROSS-REFERENCE TO RELATED APPLICATIONS

This application is a continuation of Ser. No. 13/896,778, filed 17 May 2013, which is a continuation of U.S. Ser. No. 12/348,868, filed 5 Jan. 2009, which is a continuation of U.S. Ser. No. 10/796,288, filed 10 Mar. 2004, which claims benefit of U.S. Ser. No. 60/452,956, filed 10 Mar. 2003. The contents of each application recited above are incorporated herein by reference in their entirety.

FIELD OF THE INVENTION

The present invention provides methods of processing histopathologically processed biological samples, tissue, and cells into a biomolecule lysate that is suitable for multiple uses. The methods allow extraction, isolation, solubilization, and storage of biomolecules from the lysates, including proteins, glycoproteins, nucleic acids, lipids, glycolipids, and cell organelle-derived molecules. This multi-use biomolecule lysate is soluble, dilutable, capable of being fractionated, and usable in any number of subsequent biochemical assays.

BACKGROUND OF THE INVENTION

For over a hundred years, public and academic medical universities and institutions, pathology clinics, private biomedical institutions, tissue archives, hospitals, and museums have been preserving biological specimens with formalin and other chemical fixatives such as formaldehyde and ethyl alcohol. The most common chemical fixative is formalin. Formalin is used as a fixative because of its superior ability to preserve both tissue structure and cellular morphology. This has resulted in the wide use of formalin for the successful preservation of histologic sections for traditional microscopic analysis. Formalin fixation is so effective in preserving tissue structure and cellular morphology that the formalin archive is a veritable treasure trove containing millions of samples. Within this archive are biological samples of healthy tissue, tissue samples from virtually every known disease, and a multitude of preserved life forms.

The most common form of sample fixation occurs through formalin-induced cross-linking of the proteins within the biological specimen. These protein cross links, while providing excellent cellular morphology preservation, also renders the fixed sample relatively insoluble. Because of these protein cross-links, the types of assays that can be performed on a formalin-fixed sample are limited in number, unable to provide quantitative results and lack sensitivity. In fact, formalin fixed biological samples are virtually unusable in many modern assay techniques, which are both highly quantitative and sensitive.

It is apparent, therefore, that new methods for solubilizing formalin-fixed or other chemically-fixed biological samples are greatly to be desired.

SUMMARY OF THE INVENTION

An object of the present invention provides for a method to solubilize formalin-fixed biological samples. More specifically, the present invention provides for a method of obtaining a multi-use biomolecule lysate from a histopathologically processed biological sample.

In accordance with one aspect of the invention there is provided a method of preparing a multi-use biomolecule lysate, comprising the steps of: (a) heating a composition comprising a histopathologically processed biological sample and a reaction buffer at a temperature and a time sufficient to negatively affect protein cross-linking in the biological sample, and (b) treating the resulting composition with an effective amount of a proteolytic enzyme for a time sufficient to disrupt the tissue and cellular structure of the biological sample.

The histopathologically processed biological sample may comprise a substantially homogeneous population of tissues or cells. The sample may be, for example, formalin-fixed tissue/cells, formalin-fixed/paraffin embedded (FFPE) tissue/cells, FFPE tissue blocks and cells from those blocks, and/or tissue culture cells that have been formalin fixed and/or paraffin embedded.

If the sample is embedded in paraffin or some similar material, the paraffin may be removed by, for example, adding an organic solvent, heating; heating and adding a buffer comprising Tris, and/or heating and adding an organic solvent. Advantageously this step is carried out prior to the main heating step. If the sample is heated as part of the process to remove paraffin, the heating need only be brief, for example a few minutes. This brief heating advantageously may be repeated two or more times to ensure maximum removal of paraffin.

At any stage, the sample may be mechanically disrupted by, for example manual homogenization; vortexing; and/or physical mixing. The lysate produced by these methods may be subjected to a wide variety of biochemical assays. The lysate also may be fractionated, for example into nucleic acid and protein fractions, before assay. Each biomolecule fraction typically contains distinct and separate biomolecules that are suitable for use in biochemical assays.

The heating step may be carried out, for example, at a temperature between about 80° C. and about 100° C. and for a period of from about 10 minutes to about 4 hours. The proteolytic enzyme treatment lasts, for example, for a period of time from about 30 minutes to about 24 hours. The proteolytic enzyme treatment may be carried out, for example, at a temperature between about 37° C. to about 65° C. In each step, the reaction buffer may comprise a detergent, and/or a detergent may be added after the protease treatement. The detergent may be, for example, Nonidet P40™, SDS, Tween-20™, Triton X™, and/or sodium deoxycholate, although the skilled artisan will recognize that other detergents may be used. The proteolytic enzyme may be for example, proteinase K, chymotrypsin, papain, pepsin, trypsin, pronase, and/or endoproteinase Lys-C, although the skilled artisan will recognize that other enzymes may be used. The reaction buffer may comprise Tris and may have a pH in the range of about 6.0 to about 9.0.

It is a further object of the invention to provide a kit for preparing a multi-use biological lysate, where the kit contains (a) histopathologically processed biological sample, (b) a proteolytic enzyme, and (c) a detergent.

It is yet another object of the invention to provide methods of detecting one or more analytes in a multi-use biomolecule lysate suspected of containing the one or more analytes, comprising the steps of: (a) contacting a multi-use biomolecule lysate as described above with an array, where the array comprises one or more capture agents of known binding specificity immobilized on a support surface in a positionally distinguishable manner; and (b) detecting the binding or absence of binding of one or more analytes in the lysate to the immobilized capture reagents. One or more of the analytes may be, for example, a protein. The capture reagents may be, for example, antibodies and antibody fragments, single domain antibodies, engineered scaffolds, peptides, nucleic acid aptamers, a receptor moiety, affinity reagents, small molecules such as, for example, drugs, and protein ligands, although other capture reagents also could be used. The support surface may be, but is not limited to, for example, a material selected from the group consisting of glass, derivitized glass, silicon, derivitized silicon, porous silicon, plastic, nitrocellulose membranes, nylon membranes, and PVDF membranes. One or more of the analytes may be a nucleic acid or a nucleic acid, such as RNA or DNA. The multi-use biomolecule lysate may be subjected to a fractionation step prior to contacting the lysate with the array.

It is a still further object of the invention to provide methods of analyzing two or more multi-use biomolecule lysates obtained from two or more histopathologically processed biological samples, comprising the steps of (a) immobilizing two or more multi-use biomolecule lysates obtained from a histopathologically processed sample on a support surface, where each lysate is immobilized at a discrete location on the surface; (b) contacting the support surface with a reagent of known binding affinity; and (c) detecting the presence or absence of binding of the reagent of known binding affinity at the discrete locations on the support surface. In a particular embodiment, the detecting step (b) may be carried out using a detection reagent that specifically binds to one or more of the analytes suspected to be present in the sample. The lysate may be fractionated prior to immobilization on the surface. For example, the RNA, DNA, and/or protein fractions of the lysate may be immobilized on the surface.

The lysate may be spotted onto the support surface by, for example, manual spotting, ink-jetting, robotic contact printing, robotic non-contact printing and/or piezoelectric spotting. The reagent of known binding affinity may be, for example, an antibody or antibody fragments, a single domain antibody, an engineered scaffolds, a peptide, a nucleic acid aptamer, a receptor moiety, an affinity reagent and/or a protein ligand. The support surface may be, but is not limited to, for example, a material selected from the group consisting of glass, derivitized glass, silicon, derivitized silicon, porous silicon, plastic, nitrocellulose membranes, nylon membranes, and PVDF membranes.

BRIEF DESCRIPTION OF THE DRAWINGS

The present invention will be better understood with reference to the appended drawing sheets wherein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides methods for treating histopathologically processed biological samples in a manner that allows the samples to be used in a wide variety of biochemical assays. For example, the methods of the invention permit for the first time the recovery of proteins and nucleic acids from histopathologically processed biological samples in a form that is useful for further assays.

Specifically, the present inventors have surprisingly found that histopathologically processed biological samples can be heated in a reaction buffer, followed by protease treatment, to provide lysates that are rich in molecular information regarding the original biological sample. Vast numbers of histopathologically processed biological samples from a huge array of normal and diseased tissues are available in laboratories and hospitals around the world, and the methods of the present invention expand to a significant degree the information that can be obtained from those samples, as described in more detail below.

It is to be understood that the present invention is not limited to the particular methodologies, protocols, constructs, formulae and reagents described and as such may vary. It is also to be understood that the terminology used herein is for the purpose of describing particular embodiments only, and is not intended to limit the scope of the present invention.

As used herein and in the appended claims, the singular forms "a," "and," and "the" include plural reference unless the context clearly dictates otherwise. Thus, for example, reference to "a cell" is a reference to one or more cells and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the compositions and methodologies that are described in the publications that might be used in connection with the presently described invention. The publications discussed above and throughout the text are provided solely for their disclosure prior to the filing date of the present application. Nothing herein is to be construed as an admission that the inventor is not entitled to antedate such disclosure by virtue of prior invention.

Biological Samples

The present invention provides for a method of obtaining a multi-use biomolecule lysate from a histopathologically processed biological sample. Histopathologically processed biological samples can include whole organisms, samples obtained from diagnostic surgical pathology, tissue samples, body fluids, cellular or viral material, or any other biological sample that has been histopathologically processed. Uses of the multi-functional lysate include diagnostic or predictive disease modeling, but this lysate may also be used in conjunction with any useful laboratory technique as dictated by the particular circumstances.

One embodiment of the present invention provides for obtaining a multi-use biomolecule lysate from a histopathologically processed biological sample. Examples of histopathological processing of biological samples include, but are not limited, to: formalin fixation of whole organisms; formalin fixation of tissues or cells; formalin fixation/paraffin embedding of tissues or cells; and formalin fixation and/or paraffin embedding of tissue culture cells.

Histopathological processing typically occurs through the use of a formalin fixative. Formalin is used widely because it is relatively inexpensive, easy to handle, and once the formalin-fixed sample is embedded in paraffin the sample is stored easily. Additionally, formalin is often the fixative of choice because it preserves both tissue structure and cellular morphology. Although the exact mechanism may not be understood fully, fixation occurs by formalin-induced cross-linking of the proteins within the biological specimen. Due to these protein cross-links, formalin fixation has found wide success in the traditional microscopic analysis of histologic sections. Once a biological sample is histopathologically processed however, it is no longer soluble. As a result, only a few experimental techniques are available for histopathologically processed biological samples. The current assays that can be performed on a formalin-fixed sample are both few and at best, semi-quantitative. Examples of assays that can be performed on formalin fixed tissue are immunohistochemistry (IHC), in situ hybridization (ISH), and fluorescence in situ hybridization (FISH). ISH and FISH provide cellular localization of mRNA or DNA. These assays all suffer from the same shortcomings in terms of lack of quantification, low sensitivity, and difficulty in performing high-throughput assays. Formalin fixation therefore renders the formalin fixed archive of little value for many of the powerful analysis methods that have been developed in recent years.

The sheer volume of formalin-fixed specimens cannot be overstated. For nearly the last one hundred years, biological specimens have been commonly fixed in formalin or formalin fixed/paraffin wax-embedded (FFPE) blocks. Universities and museums have vast archives of plants and animals that are formalin-fixed. Hospitals, in the course of diagnostic surgical pathology, have established large formalin-fixed collections that contain tissues from nearly every known disease in addition to normal, healthy tissue. Due to the need to retain these clinical tissue samples in case further testing is required, these archives around the world now contain millions of FFPE samples.

One embodiment of the invention described herein provides for the creation of a soluble multi-use biomolecule lysate from histopathologically processed biological samples. This method includes making a multi-use biomolecule lysate directly from a histopathologically preserved biological sample, e.g., a tissue or cell, allowing one to obtain, extract, isolate, solubilize, fractionate, and store substantially all of the biomolecules of various types contained within the sample. This soluble multi-use biomolecule lysate forms a representative library of all of the biomolecules as they existed within the histopathologically processed biological sample. Such biomolecules include but are not limited to proteins, glycoproteins, nucleic acids (e.g., DNA, RNA), lipids, glycolipids, and cell organelle-derived molecules.

In addition, the multi-use biomolecule lysate is malleable. For example, the multi-use biomolecule lysate may be fractionated into a nucleic acid fraction and a fraction that contains the remaining biomolecules by methods well known in the art. Furthermore, this multi-use biomolecule lysate is capable of being serially diluted. Another embodiment of the present invention provides for a method wherein a multi-use biomolecule lysate from a histopathologically processed biological sample may be used in a number of experimental techniques.

Uses of the Lysates

The method described herein is particularly useful because it can be used to obtain a multi-use biomolecule lysate from a histopathologically processed biological sample capable of being used with numerous experimental and diagnostic techniques, thereby providing new uses for the histopathologically processed archive. Examples of techniques that the multi-use biomolecule lysate can be used with include but are not limited to are chromatography, protein arrays, Western blotting, immunoprecipitation, affinity columns, alternative splicing assays, mutation analysis, nucleic acid amplification, labeled probes for microarray analysis, RFLP analysis, Southern blotting, and high-throughput assays such as but not limited to one- and two-dimensional polyacrylamide gel electrophoresis (2D-PAGE), serial analysis of gene expression (SAGE), HPLC, FPLC, MALDI-TOF mass spectroscopy, SELDI mass spectroscopy, liquid chromatography, mass spectrometry, ELISA assays, Quantitative RT-PCR, Single Nucleotide Polymorphism detection, genotyping and sequencing. The skilled artisan will recognize that the lysates produced by the methods of the invention also may be used in a wide variety of additional assays.

The recent completion of the Human Genome Project, in addition to spurring dramatic advances in the field of genomics and proteomics, has demonstrated the vast potential of high throughput assays. Proteomics has gone beyond its initial attempts to identify and quantify proteins and is now attempting to determine the functions of all proteins in an organism, organ, or organelle, and how these proteins vary with time and physiological state.

"Functional genomics" attempts to determine the physiological role of each gene. An important step in discovering the function of each gene is to carefully measure the expression patterns of mRNA transcripts and proteins in tissue specimens. By measuring specific expression patterns of genes and gene products such as mRNA and proteins, one can determine what genes are expressed and at what levels in a normal, healthy cell type. Perhaps more importantly however, is that by measuring the expression patterns in diseased cell types, new insight will be gleaned into the pathological progression of that disease. In addition, new markers may be discovered, thereby yielding new diagnostic and therapeutic strategies.

The ability to utilize the formalin fixed archive would be a tremendous aid in these undertakings. Often times, patient outcome is known for each pathological specimen. Correlations between markers and patient prognosis therefore could be readily created. In addition, because the multi-use biomolecule lysate is a representative library of the histopathologically processed biological sample, both nucleic and non-nucleic fractions are present. Therefore, direct relationships between nucleic acid expression and the presence of non-nucleic acid molecules can be determined. This is an advantage over current techniques that isolate only the nucleic acid fraction or the non-nucleic acid fraction and only indirect correlations may be drawn. Alternatively, high-throughput assays are a boon to comparative and evolutionary biologists and zoologists due to the ability of these assays to generate and quantify differences between species. The scope of these undertakings is only possible through the use of high-throughput assays.

Array Assays

A specific example of a high-throughput assay is the protein array. Protein arrays are highly parallel (multiplexed) and can be conducted in miniature (microarray). Protein arrays are quick, usually automated, highly sensitive, and capable of generating an enormous amount of data in a single experiment. The protein array is essentially a miniaturized version of the familiar ELISA or dot blotting immunoassay. Similar to ELISA and dot blots, protein array results are usually obtained using optical detection methods, for example fluorescent detection. The data generated by a single protein array experiment often is so voluminous that specialized computer software may be required to read and analyze the data that is generated.

High-throughput assays such as protein array analysis are capable of screening vast amounts of biological samples at once. In order to significantly link a single candidate marker to any disease, a large number of cases must be screened to generate definite correlations. However, obtaining enough biological samples with known disease outcomes in a frozen or stable and storable state that is not chemically fixed is a limiting factor. A possible solution to this limitation would be the use of the archive of formalin-fixed tissues and cells. The methods of the current invention are particularly useful because the multi-use biomolecule lysate allows the formalin-fixed tissue archive to be used in high-throughput protein array analysis.

In one type of protein array analysis, specific capture reagents of known binding affinity, such as antibodies, are immobilized or spotted onto a support surface in a known positional manner, thus forming the protein array. Plasma, other tissue extracts, or in this case the multi-use biomolecule lysate is then added to the protein array. Because the immobilized binding proteins on the support surface have a specific affinity for an individual protein or marker, protein arrays are able to detect target molecules or marker proteins in the specimen. By immobilizing the specific capture reagents in known locations on the support surface, protein identification and the presence of marker proteins can be determined by x, y positional information. In addition, since differences in protein levels within complex samples can be easily measured, accurate quantitative differential analysis can also be performed. Detection is achieved through a number of methods known to those well versed in the art. Examples include but are not limited to: secondary antibodies in sandwich assays, direct labeling of analytes, dual color labeling, mass spectrometry, surface plasmon resonance, and atomic force microscopy.

An alternative type of protein array analysis places tissue/cell lysates in an arrayed format, for example on a solid support. Multiple lysates from different samples may be arrayed on a single surface in a positionally identifiable manner. Reagents of known binding specificity, such as antibodies, that bind to target biomolecules or markers are then added. The main difference between the two major types of array analyses described herein is that in the first type of protein array, the expression of many different proteins across a single source of protein (a single cancer tissue for example) can be determined. In contrast, by the other type of protein array analysis, one can assay for the expression of one protein at a time across many different sources of protein (many different cases of cancer tissues for example). The lysate may be fractionated prior to immobilization on the array, and protein containing fractions of the lysates may be used to prepare the array. The skilled artisan will recognize also that other fractions of the lysates can be used to prepare arrays. For example, DNA and/or RNA containing fractions can be immobilized on suitable surfaces to prepare nucleic acid arrays.

Specific reagents of known binding affinity in protein arrays advantageously are antibodies or antibody fragments, but may also be single domain antibodies, engineered scaffolds, peptides, nucleic acid aptamers, small molecules such as drugs, for example, protein ligands, or other specific binding proteins known in the relevant art. Antibodies may be either polyclonal or monoclonal, or a portion or fragment of an antibody capable of binding antigenic sites, and are available from the usual commercial sources such as Sigma-Aldrich Co. (St. Louis, Mo.).

Protein array support surfaces include but are not limited to glass (such as slides), silicon, porous silicon, nylon, PVDF or nitrocellulose membranes and the like, or beads and are available from a variety of commercial sources. Alternatively, specialized chips have been developed for protein assays and are commercially available from, for example, Biotrove (Woburn, Mass.), Zyomyx (Hayward, Calif.) and Pontilliste (Mountain View, Calif.).

Specific capture reagents or tissue/cell lysates can be spotted or immobilized onto the support surface by a number of techniques familiar to those knowledgeable in the arts. Examples include, but are not limited to, robotic contact printing, robotic non-contact printing, ink jetting, and piezoelectric spotting. If the capture reagent is a polymer that may be synthesized on a solid support, such as a nucleic acid, the capture reagent may be prepared directly on the support by, for example, photolithography. A number of automated commercial spotters are available from, for example, Packard Bioscience (Meriden, Conn.) and manual spotting equipment also is commercially available from, e.g. V & P Scientific (San Diego, Calif.).

As used herein, the term "analyte" refers to a biomolecule contained within the biological sample that is detectable by binding to a reagent of specific binding affinity.

As used herein, the term "buffer" refers to buffer which has a specific pH in the range of 1.0 to 9.0. Both specific pH and buffer types are selected based upon the proteolytic enzyme used. Both buffer type and specific pH requirements are known to those well versed in the arts.

As used herein, the term "organic solvent" refers to solvents for removing paraffin including but not limited to xylene, toluene, or chloroform.

As used herein, the term "incubate" refers to bringing a reagent of known binding affinity in contact with the biological sample in order to facilitate binding between the reagent of known specific binding affinity and analytes contained in the biological sample. Incubation time and reagent concentration need only be sufficient to obtain a desired result, although the skilled artisan will recognize that both incubation time and reagent concentration may be optimized using methods that are known in the art once suitable reagents have been identified.

As used herein, the term "sufficient homogeneity" refers to a population of tissues or cells that possess similar characteristics or traits based on selection criteria. An example of selection criteria includes but is not limited to histopathological selection criteria that are well known in the relevant arts. Examples of methods of actually "obtaining" a biological sample include but are not limited to using a manual core punch, tissue punch, laser microdissection and other techniques that are well known in the arts. The actual size of the obtained biological sample is not important as long as there is a sufficient amount to perform the chosen assay.

Methods of Preparing Lysates

The methods of the present invention involve heating the histopathologically processed biological sample for a time and at a temperature sufficient to negatively affect the formalin-induced protein cross-links. The skilled artisan will recognize that time and temperature of heating are not critical and may be varied, though a typical period for heating is from about 30 minutes to about 24 hours. The mechanisms by which temperature may negatively affect the formalin-induced cross-links include but are not limited to reversing of the protein cross-links. Although the exact mechanism is not known, and without being bound by any theory, the present inventors believe that the negative affect of temperature on the protein cross-links appears to involve some form of releasing, reversing, or partial modification of the cross-links.

The method of the present invention further involve adding at least one proteolytic enzyme to the histopathologically processed biological sample. Proteolytic enzymes are believed to augment the negative effect of heating on formalin-induced protein cross-links. The time, temperature, and quantity of the proteolytic enzyme are not critical as long as they are all sufficient to negatively affect the formalin-induced protein cross-links. Examples of proteolytic enzymes that are suitable for use in the present invention include but are not limited to trypsin, proteinase K, chymotrypsin, papain, pepsin, pronase, and endoproteinase Lys-C. Trypsin may be purchased from Sigma-Aldrich (St. Louis, Mo.). Advantageously, the protease treatment is carried out following the heating step described above. The protease treatment is advantageously carried out at a temperature that is optimal for maximum activity of the protease, but this can be varied.

In one embodiment of the current invention, the multi-use biomolecule lysate may be fractionated into distinct and separate biomolecules that may be collected separately. Examples of biomolecule fractions that can be collected include but are not limited to protein, glycoproteins, nucleic acids (e.g., DNA, RNA), glycolipids, and lipids. Fractionation techniques are well known in the arts and include but are not limited to, spin column fractionation, immunoprecipitation, gradient centrifugation, HPLC and drip column fractionation. Other fractionation methods are well known in the art.

After fractionation, the desired fraction of the multi-use biomolecule lysate may be used in subsequent assays. Examples of assays that biomolecule fractions of the multi-use biomolecule lysate can be used with include but are not limited to are column chromatography, protein arrays, Western blotting, immunoprecipitation, affinity columns, alternative splicing assays, mutation analysis, nucleic acid amplification (for example PCR, LCR, and T7 based RNA amplification), labeled probes for microarray analysis, RFLP analysis, Southern blotting, and high-through put assays such as but not limited to one- and two-dimensional polyacrylamide gel electrophoresis (2D-PAGE), serial analysis of gene expression (SAGE), HPLC, FPLC, MALDI-TOF mass spectrometry, SELDI mass spectrometry, liquid chromatography, mass spectrometry, ELISA assays, Quantitative RT-PCR, Single Nucleotide Polymorphism detection, genotyping and sequencing.

Figure 1:
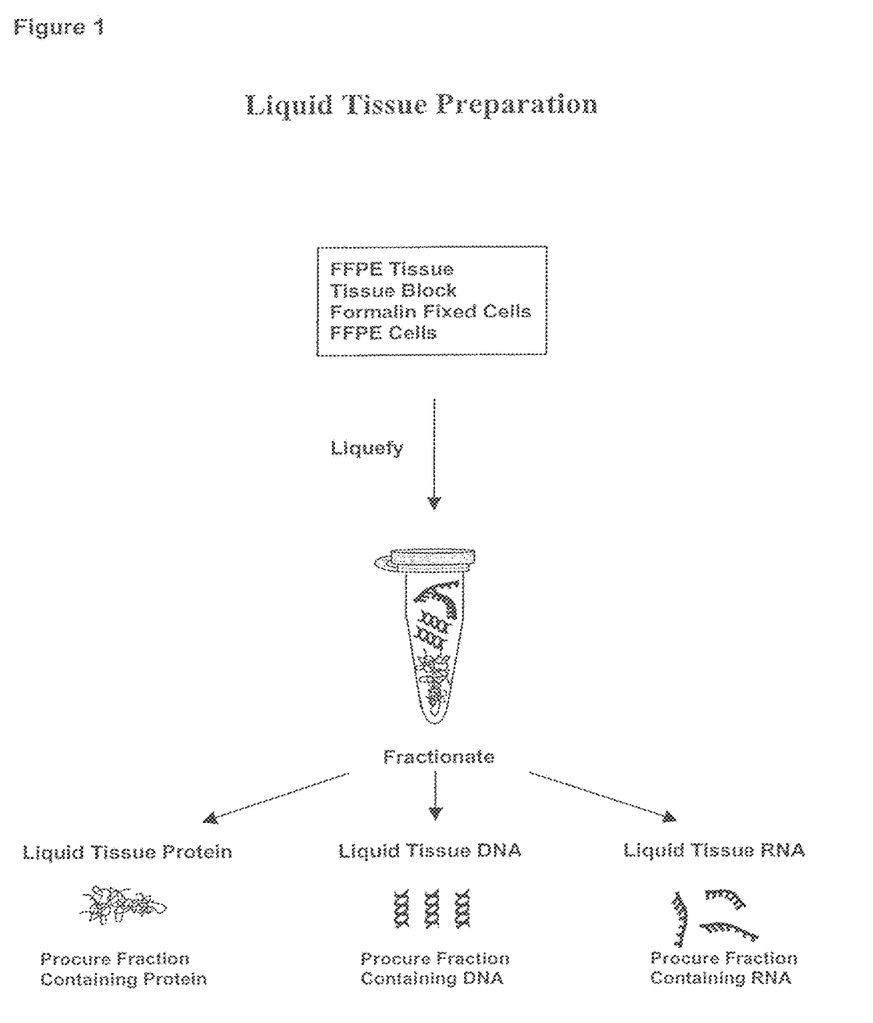
FIG. 1 is a flow chart illustrating the method of the multi-use biomolecule lysate preparation of the present invention.
Figure 2:
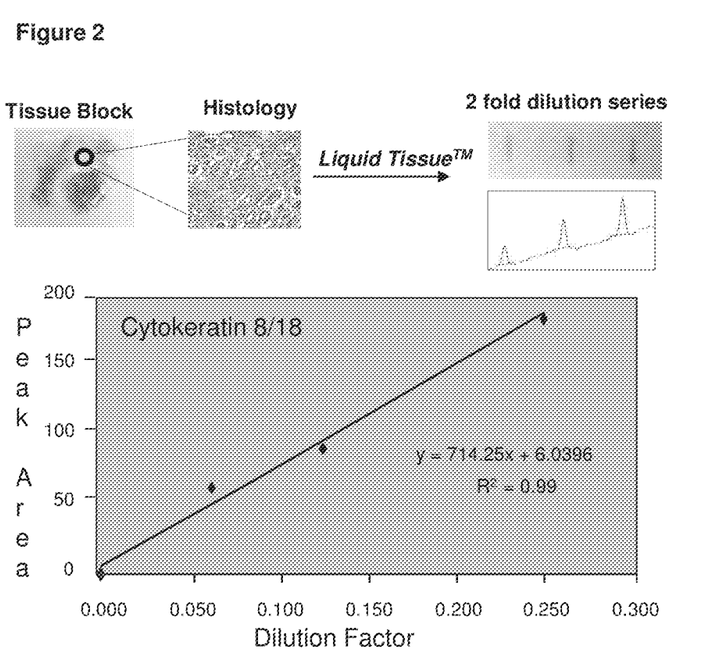
FIG. 2 shows a typical protein expression analysis and demonstrates that a multi-use biomolecule lysate preparation is dilutable and can be used for quantitative protein expression profiling of cells obtained from formalin fixed tissue samples.
Figure 3:
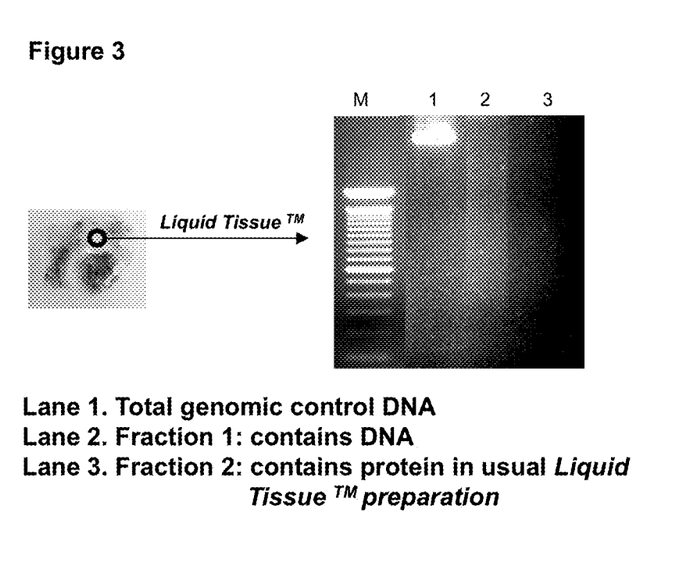
FIG. 3 shows a standard multi-use biomolecule lysate preparation that was fractionated. Both fractions were recovered and used for gel electrophoresis analysis for nucleic acid determination.

The present invention includes articles of manufacture, such as "kits." Such kits will typically be specially adapted to contain in close compartmentalization each container holding a component useful in carrying out the preparation of the multi-use lysate according to the methods and compositions taught herein. In a particular embodiment, the present invention provides compositions that contain a histopathologically processed biological sample, a reaction buffer, and a detergent. The kit may further include a protease, and a reagent for removing paraffin from the sample, such as a buffer and/or an organic solvent FIG. 1 is a flow chart illustrating an embodiment of the present invention, comprising a method of preparing the multi-use biomolecule lysate and subsequently utilizing said lysate in a number of different assays. These "steps" need not be performed in any particular order, and serve as a non-limiting description as follows:

(a) applying specific selection criteria, based on histology, to a biological sample to achieve an enrichment of specific homogeneous biological tissue/cell populations. The enrichment can be carried out, for example, by tissue microdissection methods, before biomolecule procurement in the form of liquid tissue preparation;

(b) adding a specific pH-adjusted (ranging from pH 6.0 to pH 9.0) Tris-based buffer to said procured biological sample for stabilization of peptides, peptide fragments, proteins, enzymes, DNA, DNA fragments, RNA, RNA fragments, and other biomolecules and biomolecule fragments;

(c) imparting some level of physical disruption to the biological sample by a method that includes but is not limited to manual homogenization, vortexing, and/or physical mixing;

(d) heating the biological sample at an elevated temperature in the range of from about 80° C. to about 100° C. for a period of time from about 10 minutes to about 4 hours. Temperature range and time period may be determined by those of skill in the art, based for example, on sample size; (e) adding one or more proteolytic enzyme(s) including for example proteinase K, chymotrypsin, papain, pepsin, trypsin, pronase, and endoproteinase Lys-C to the biological sample for a period of time from about 30 minutes to about 24 hours at an elevated temperature from about 37° C. to about 80° C., advantageously at a temperature from about 37° C. to about 65° C. The temperature range and time may be determined by skilled artisans considering, for example, the size of the biological sample and/or the chosen proteolytic enzyme;

(f) adding one or more detergents including for example Nonidet P40™, SDS, Tween-20™, Triton X™ and sodium deoxycholate to the biological sample. The detergent may be added prior to the protease treatment step (before or after heating), in which case the nature of the detergent and its concentration is selected so as to not substantially inhibit the activity of the protease, or may be added after the protease step;

(g) molecularly fractionating the resulting biological sample by some method as for example spin column fractionation, immunoprecipitation, gradient centrifugation, HPLC, and drip column fractionation in order to separate specific molecular fractions, resulting in the procurement of different biomolecules in different and collectable fractions;

(h) procuring and purifying specific subcellular and molecular fractions for the procurement of different biomolecules for subsequent biochemical assays.

In the present invention, each lysate of biomolecules forms a representative library of specific biomolecules that directly reflects the status of those biomolecules as they previously resided in the histopathologically processed biological sample. An example of such a representative biomolecular lysate library from histopathologically processed biological sample would be the preparation of a lysate of proteins directly from formalin-fixed paraffin embedded tissue/cells.

The resulting preparation of biomolecules can be placed in an arrayed format for the simultaneous biochemical analysis of multiple liquid tissue preparations (multi-use biomolecule lysate) obtained from multiple and different histopathologically processed biological samples. An example of such a high throughput array assay format would be the development of a liquid tissue protein array such that tissue protein lysates derived from histopathologically processed samples and procured as stated above are arrayed in an ordered and defined pattern as small spots of protein on a solid support substrate, where each spot is a representative library of the expressed proteins, and characteristics of those expressed proteins, that resided in the histopathologically processed biological sample, and that when assayed by a number of various biochemical protein analysis formats, such as immuno-based protein identification binding assays, do directly reflect the expression pattern and characteristic of the proteins as they relate to the pathology and histology of the histopathologically processed biological sample from which the proteins were procured.

When the biomolecule of interest is a protein, the protein extract is in a soluble liquid form and is representative of the total protein content of the cells procured from the starting histopathologically processed biological sample. The protein extract can be placed in any number of protein identification, analysis and expression assays including but not limited to liquid tissue protein microarrays that contain representative libraries of proteins from pathologically and histologically defined populations of histopathologically processed biological sample and as these analyses relate to the histology, disease state, and pathology of the histopathologically processed biological sample.

When the biomolecule is DNA, the DNA extract is in a soluble liquid form and is representative of the total DNA content of the cells procured from the starting histopathologically processed biological sample. The DNA extract can be placed in any number of DNA and/or RNA gene identification analyses and monitoring assays designed to determine variations in DNA including but not limited to the analysis of gene structure, genetic variability, single nucleotide polymorphisms and mutation analyses as these analyses relate to the histology, disease state, and pathology of the histopathologically processed biological sample.

When the biomolecule is RNA, the RNA extract is in a soluble liquid form and is representative of the total RNA content of the cells procured from the starting histopathologically processed biological sample. The RNA extract can be placed in any number of RNA and/or gene identification analysis and gene expression analysis and quantitative RT-PCR analysis as these analyses relate to the pathology, disease state, and histology of the starting histopathologically processed biological sample.

When the biomolecule is a biomolecule other than protein, DNA and RNA, the biomolecule is assayed as it relates to the pathology, disease state and histology of the starting histopathologically processed biological sample.

The present invention, thus generally described, will be understood more readily by reference to the following examples, which are provided by way of illustration and are not intended to be limiting of the present invention.

Example 1. Preparation of a Multi-Use Lysate from a Formalin-Fixed Sample

1. Place one 2 mm diameter by 25 μm thick section from a tissue punch into a silanized or low protein binding 1.5 ml microcentrifuge tube.
2. Add 500/μl of 20 mM Tris-HCl pH 7.8.
3. Heat at 95° C. for 1 minute.
4. Mix gently on a vortex mixer.
5. Carefully, without disturbing the tissue section, remove the buffer using a pipettor.
6. Add 750 μl of 20 mM Tris-HCl pH 7.8.
7. Heat at 95° C. for 1 minute.
8. Carefully, without disturbing the tissue section, remove the buffer using a pipettor.
9. Microcentrifuge at 10,000 rpm for 1 minute.
10. Remove any residual buffer from the microcentrifuge tube with a pipettor.
11. Add 10 μl of reaction buffer (10 mM Tris-HCl pH 7.8, 1.5 mM EDTA, 0.1% Triton X-100, 10% glycerol) to the tube. Make sure that the tissue is at the bottom of the tube and covered with reaction buffer.
12. Heat at 95° C. for 1.5 hours. Every 20 minutes, check the tube and shake the buffer that has formed a condensation in the cap down to the bottom of the tube so that it covers the tissue section before placing the tube back into the heating block.
13. Microcentrifuge at 10,000 rpm for 1 minute.
14. Place tubes on ice to cool.
15. Add 0.5 μl of 1% Trypsin and gently mix.
16. Incubate for 1 hour at 37° C. Every 20 minutes check the tube and shake the buffer that has formed a condensate in the cap down to the bottom of the tube. Vortex rigorously for 10 to 15 seconds. Shake the buffer down to the bottom of the tube so that it covers the tissue section before placing the tube back into the waterbath.
17. Microcentrifuge at 10,000 rpm for 1 minute.
18. Heat at 95° C. for 5 minutes.
19. Microcentrifuge at 10,000 rpm for 1 minute.

The resulting multi-use biomolecule lysate may be either used in subsequent assays or stored at −20° C. until ready for use.

While there has been described what is presently believed to be the preferred embodiments of the present invention, other and further modifications and changes may be made without departing from the spirit of the invention. We intend to include all further and other modifications and changes that come within the scope of the invention as set forth in the claims.

What is claimed is:

1. A method of preparing a multi-use biomolecule lysate, comprising the steps of:
   (a) heating a composition comprising a histopathologically processed biological sample and a reaction buffer at a temperature and a time sufficient to negatively affect protein cross-linking in said biological sample, wherein the temperature is at least 80° C. and the period of time is up to 24 hours; and
   (b) treating the resulting composition with an effective amount of one or more proteolytic enzymes for a time sufficient to disrupt the tissue and cellular structure of said biological sample and to liquefy said sample, thereby producing a liquid, soluble, dilutable biomolecule lysate wherein the protein content of said lysate is representative of the total protein content of said histopathologically processed biological sample.

2. The method according to claim 1, wherein said histopathologically processed biological sample comprises a substantially homogeneous population of tissues or cells.

3. The method according to claim 1, further comprising, prior to step (a), the step of removing any paraffin present in said histopathologically processed biological sample by one or more methods selected from the group consisting of: adding an organic solvent;

heating; heating and adding a buffer comprising Tris; and heating and adding an organic solvent.

4. The method according to claim 1, further comprising prior to step (a) the step of mechanically disrupting said biological sample by at least one technique selected from the group consisting of: manual homogenization; vortexing; and physical mixing.

5. The method according to claim 1, wherein said biological sample is heated to a temperature between about 80° C. and about 100° C.

6. The method according to claim 1, wherein said biological sample is heated for a period of time from about 10 minutes to about 4 hours.

7. The method according to claim 1, wherein said proteolytic enzyme treatment is carried out at a temperature between about 37° C. to about 65° C.

8. The method according to claim 1 wherein said reaction buffer comprises a detergent.

9. The method according to claim 1 further comprising the step of fractionating said multi-use biomolecule lysate into distinct and separate biomolecule fractions.

* * * * *